(12) United States Patent
Roehri et al.

(10) Patent No.: US 11,944,445 B2
(45) Date of Patent: Apr. 2, 2024

(54) METHOD FOR DETECTING ELEMENTS OF INTEREST IN ELECTROPHYSIOLOGICAL SIGNALS AND DETECTOR

(71) Applicants: UNIVERSITÉ D'AIX-MARSEILLE (AMU), Marseilles (FR); INSTITUT NATIONAL DE LA SANTÉ ET DE LA RECHERCHE MÉDICALE, Paris (FR); ASSISTANCE PUBLIQUE—HÔPITAUX DE MARSEILLE (AP-HM), Marseilles (FR)

(72) Inventors: Nicolas Roehri, Marseilles (FR); Christian George Benar, Plan de Cuques (FR); Fabrice Bartolomei, Roquevaire (FR)

(73) Assignees: UNIVERSITÉ D'AIX-MARSEILLE (AMU), Marseilles (FR); INSTITUT NATIONAL DE LA SANTÉ ET DE LA RECHERCHE MÉDICALE, Paris (FR); ASSISTANCE PUBLIQUE—HÔPITAUX DE MARSEILLE (AP-HM), Marseilles (FR)

(*) Notice: Subject to any disclaimer, the term of this patent is extended or adjusted under 35 U.S.C. 154(b) by 583 days.

(21) Appl. No.: 16/080,719

(22) PCT Filed: Feb. 28, 2017

(86) PCT No.: PCT/EP2017/054574
§ 371 (c)(1),
(2) Date: Oct. 17, 2018

(87) PCT Pub. No.: WO2017/148900
PCT Pub. Date: Sep. 8, 2017

(65) Prior Publication Data
US 2019/0029550 A1    Jan. 31, 2019

(30) Foreign Application Priority Data

Feb. 29, 2016  (FR) ..................................... 1600332

(51) Int. Cl.
*A61B 5/374* (2021.01)
*A61B 5/00* (2006.01)
(Continued)

(52) U.S. Cl.
CPC .............. *A61B 5/374* (2021.01); *A61B 5/316* (2021.01); *A61B 5/369* (2021.01); *A61B 5/4094* (2013.01); *A61B 5/726* (2013.01); *A61B 5/7264* (2013.01)

(58) Field of Classification Search
CPC ......... A61B 5/374; A61B 5/369; A61B 5/316; A61B 5/4094; A61B 5/726; A61B 5/7264;
(Continued)

(56) References Cited

U.S. PATENT DOCUMENTS

| | | | |
|---|---|---|---|
| 2010/0204604 A1* | 8/2010 | Liley | G06K 9/00496 600/544 |
| 2012/0245481 A1 | 9/2012 | Blanco et al. | |

(Continued)

FOREIGN PATENT DOCUMENTS

| | | |
|---|---|---|
| CN | 102488516 A | 6/2012 |
| CN | 104000587 A | 8/2014 |

(Continued)

OTHER PUBLICATIONS

Dempster, John. Computer Analysis of Electrophysiological Signals. Biological Techniques Series, Academic Press. (Year: 1993).*
(Continued)

*Primary Examiner* — Patrick Fernandes
(74) *Attorney, Agent, or Firm* — Seckel IP, PLLC (57) ABSTRACT

A method for automatically detecting elements of interest in electrophysiological signals includes: delivering electrophysiological signals; producing a whitened time-frequency representation of the electrophysiological signals; setting a
(Continued)

threshold; applying this threshold to the whitened time-frequency representation; and, in the whitened time-frequency representation, detecting local maxima that are higher than or equal to the applied threshold.

23 Claims, 7 Drawing Sheets

(51) Int. Cl.
    *A61B 5/316*     (2021.01)
    *A61B 5/369*     (2021.01)

(58) Field of Classification Search
    CPC ....... A61B 5/0006; A61B 5/291; A61B 5/318; A61B 5/378; A61B 5/7265; G06F 2218/00; G16H 15/00; G16H 50/20
    See application file for complete search history.

(56) References Cited

U.S. PATENT DOCUMENTS

| | | | |
|---|---|---|---|
| 2014/0058241 A1* | 2/2014 | Apparies | A61B 3/113 600/383 |
| 2015/0282755 A1* | 10/2015 | Deriche | A61B 5/0402 600/301 |

FOREIGN PATENT DOCUMENTS

| | | | | |
|---|---|---|---|---|
| CN | 105286860 A | * | 2/2016 | |
| JP | 2003135414 A | | 5/2003 | |
| WO | WO-0122672 A1 | * | 3/2001 | ........... H04B 1/7174 |

OTHER PUBLICATIONS

Van Vugt, Marieke. Comparison of spectral analysis methods for characterizing brain oscillations. Journal of Neuroscience Methods. 162, p. 49-63. (Year: 2007).*

Sadowsky, John. "The continuous wavelet transform: a tool for signal investigation and understanding." Johns Hopkins APL Technical Digest 15: 306-306. (Year: 1994).*

"Regression: Standardized Coefficients", Georgia Southern University, EDUR 8132 (Year: 2010).*

Van Vugt et al., "Comparison of spectral analysis methods for characterizing brain oscillations", Journal of Neuroscience Methods, vol. 162, 2007, pp. 49-63; cited in the ISR.

Hamaneh et al., "Automated Removal of EKG Artifact From EEG Data Using Independent Component Analysis and Continuous Wavelet Transformation", IEEE Transactions on Biomedical Engineering, vol. 61, No. 6, Jun. 2014, pp. 1634-1641; cited in the ISR.

Lage-Castellanos et al., "False discovery rate and permutation test: An evaluation in ERP data analysis", Statistics in Medicine, vol. 29, 2010, pp. 63-74; cited in the ISR.

Grandchamp et al., "Single-trial normalization for event-related spectral decomposition reduces sensitivity to noisy trials", Frontiers in Psychology, vol. 2, Article 236, Sep. 2011, 13 pages; cited in the ISR.

Burnos et al., "Human Intracranial High Frequency Oscillations (HFOs) Detected by Automatic Time-Frequency Analysis", PLOS ONE, vol. 9, Issue 4, Apr. 2014, 12 pages; cited in the Specification.

International Search Report and Written Opinion dated May 8, 2017 issued in corresponding application No. PCT/EP2017/054574; w/ English partial translation and partial machine translation (24 pages).

Chinese Office Action and Search Report dated Nov. 11, 2020 in corresponding application No. CN 201780026468; with English translation (total 19 pages) (D1, Van Vugt 2006 cited in the Chinese Office Action, and D3, US20120245481 cited in the Chinese Search Report, are not listed in this IDS since they were already listed in the IDS filed Aug. 29, 2018).

Zhang et al., "Research of Signal Enhancement Based on Threshold Algorithm of Free Distributed FDR Hypotheses Testing", Journal of Wuhan University of Technology, vol. 31, No. 6, Mar. 2009, pp. 114-118 (with English machine translation; total 10 pages) (D2 cited in the Chinese Office Action).

* cited by examiner

METHOD FOR DETECTING ELEMENTS OF INTEREST IN ELECTROPHYSIOLOGICAL SIGNALS AND DETECTOR

FIELD OF THE INVENTION

This invention relates to a method for detecting elements of interest in electrophysiological signals and, more particularly, in intracranial signals. It further relates to a detector for the implementation of such a method.

PRIOR ART

Electrophysiology is the study of the electrical and electrochemical phenomena that are produced in the cells or tissues of living organisms. It entails measuring the differences in electrical voltages or currents at different biological scales, from an isolated ion channel to entire organs. In neurosciences, electrophysiology studies the electrical activity of neurons or, more broadly, the electrical and magnetic activity of the nervous system, by means of electroencephalography and magnetoencephalography.

Intracerebral electroencephalography is an invasive method for recording the activity of the brain. This method is used in neurology, for example in the framework of a pre-surgical assessment in preparation for an operation aiming to remove, via exeresis, epileptogenic tissues. Similar to surface electroencephalography in that it measures the electrical potential variations due to the electrophysiological activity of neurons, intracranial electroencephalography is distinguished from it by the fact that the electrodes are positioned either on the surface of the pia mater, under the dura mater, or under the meninges directly on the cortical surface (electrocorticography, ECoG), or, finally, inside the very brain tissue by means of deep-implanted electrodes according to a stereotactic method (stereo-electroencephalography, SEEG).

The electrophysiological signals are formed by a mixture of oscillations at multiples frequencies and more transient activities. In physiological rhythms, the most present oscillation is the alpha rhythm, observed in calm wakefulness. The markers of the various phases of sleep are elements of varied forms. In pathology, electrophysiology remains the reference method for observing epileptic discharges, points or high-frequency oscillations (HFOs), of which the frequency is between 80 and 500 Hz and even higher. These high-frequency oscillations can be divided into three categories. These are so-called High-Gamma (HG) oscillations, which have a frequency between 80 and 150 Hz, oscillations of the ripple (R) type, which have a frequency between 150 and 250 Hz), and so-called fast ripple (FR) oscillations, which have a frequency between 250 and 500 Hz.

The visual analysis of these signals is long and difficult. Indeed, the signals of interest can be of very low amplitude. In addition, the analysis has great variability from one human operator to another.

It has therefore been sought to develop methods for representation and detection, as well as associated detectors, able to automatically detect elements of interest, such as transient activities or oscillatory activities, through the entire frequency range of electrophysiological signals.

A first difficulty for an automatic detector is that the transient and oscillatory activities overlap in frequency. Simple filtering is therefore insufficient.

A potential solution is to conduct a time-frequency analysis. However, this analysis comes up against a second difficulty, which comes from the fact that the signals have much more energy at low frequency than at high frequency (spectrum in $1/f^\alpha$).

A third difficulty comes from the adjusting of a threshold for automatic detection, which should be as independent as possible from the human user.

Patent document published under number US2012/0245481A1 discloses a detector, that identifies certain high-frequency oscillations in an encephalographic signal of the ECoG type. This detector filters a signal of which the frequency is between 80 and 500 Hz and calculates the energy of this signal in a sliding window. In a first step proposed in this document, application is made of the detection algorithm of Staba et al., 2002. All of the activities that exceed a certain energy threshold are then selected. However, this first step suffers from an excessively high number of false detections. That is the reason why a subsequent step is implemented, which consists in quantifying the preponderance of the signal in relation to a baseline defined over several hundred milliseconds, before and after each event detected. At the end of this subsequent step, the events that have a statistical similarity that is too close to the model of the baseline are rejected. Finally, a last step consists in extracting different parameters from the selected events, conducting a dimensionality reduction, then in grouping these events together in an unsupervised manner, into four groups.

The data is filtered in a wide frequency band. The impact of the spectrum in $1/f^\alpha$ is always very substantial because the band of the filter, between 80 and 500 Hz, is very wide. A high-frequency oscillation, in particular higher than 250 Hz, will have to be very powerful in order to pass the first threshold. Many oscillations can be missed. In addition, the first step selects all of the pointed transients, which are then grouped together. A major disadvantage is that this method does not handle complex events, i.e. events of different types that take place at the same time. However, the high-frequency oscillations almost always rise above an epileptic point. As such, the method described in this document appears to be missing many high-frequency oscillations. Note that the definition of the baseline of this technique assumes that the events of interest are separated over time, by at least about 600 ms, which is not always the case. These periods before and after the event do not necessarily correspond to a baseline.

The document entitled "Human Intracranial High Frequency Oscillations (HFOs) Detected by Automatic Time-Frequency Analysis", Burnos et al., Plos One, April 2014, vol. 9, describes a detector of high-frequency oscillations that implements a first step similar to the one disclosed in the aforementioned document, published under number US2012/0245481A1, namely the application of the detection algorithm of Staba et al., 2002. According to this document, the data is first filtered between 80 and 500 Hz then a threshold is applied. However, the threshold is not applied over an energy measurement of a short period of time but over the envelope of the filtered signal. This is the Hilbert transform. With a concern for limiting false detections, a second step is implemented. A time-frequency is calculated by using the Stockwell transform around events of interest. Then, the instantaneous power spectral density is measured in a smaller time window. Finally, three points from the spectrum obtained are selected: the local maximum in the band 60-500 Hz (High Frequency Peak—HiFP), the minimum/trough between 40 Hz and the frequency of the HiFP and the local maximum that is closest to the trough in the low frequencies. An event is then qualified as high-frequency oscillation if the power measured at the HiFP is indeed higher than that measured in the trough and than that measured at the low frequency peak (LoFP).

The signal is filtered between 80 and 500 Hz. The time-frequency is not used as such since there is a return to the analysis of the spectrum in order to decide whether or not there is a high-frequency oscillation. Note that it does not mention at any time the possibility of detecting points surpassed by high-frequency oscillations.

SUMMARY OF THE INVENTION

In light of the above, a technical problem that the invention proposes to resolve is to provide a method for detecting elements of interest in electrophysiological signals, as well as a detector for the implementation of such a method, that overcomes the aforementioned disadvantages of prior art, and which, in particular, transforms the background activity into white noise in order to balance the power of the activities through the frequencies, and which allows for a representation and an adequate detection of the low and high frequency oscillations and points or transients, while still retaining the information that is associated with them such as their frequency, the detection being carried out even if the events take place at the same time or at neighboring times, without a priori on the frequency bands concerned.

The solution proposed by the invention for this technical problem has for first object a method for the automatic detection of elements of interest in electrophysiological signals comprising the steps according to which: electrophysiological signals are delivered; a whitened time-frequency representation of said electrophysiological signals is produced; a threshold is set; this threshold is applied to the whitened time-frequency representation; in the whitened time-frequency representation, local maxima that are higher than or equal to the applied threshold are detected, and according to said method, for the production of the whitened time-frequency representation, a continuous wavelet transform is applied and the square modulus of the wavelet coefficients is calculated after having standardized the real and imaginary parts thereof.

It has for second object a detector for the automatic detection of elements of interest in electrophysiological signals, characterized in that it is implemented in a software in the form of an extension module, for the implementation of this method.

It has for third object the use of such a detector, for the automatic detection of elements of interest in electrophysiological signals of epileptic patients.

Advantageously, —the electrophysiological signals are intracranial signals; —the intracranial signals are stereo-electroencephalographic signals; —the elements of interest are low and high frequency oscillations and points; —the continuous wavelet transform is calculated from the following formula:

$$T_f(b, \alpha) = \frac{1}{\sqrt{\alpha}} \int_{-\infty}^{+\infty} f(t) \overline{\psi\left(\frac{t-b}{\alpha}\right)} dt$$

wherein f is the electrophysiological signal, T is the continuous wavelet transform, $\psi$ is the wavelet, a the dilation factor, b the translation factor and t is the time; —the wavelet chosen is a Gaussian derivative wavelet (DoG), analytical and its expression in the frequency domain is as follows: $\overline{\psi}(f) = f^n \exp(-f^2)$ for $f \geq 0$ and $= 0$ for $f < 0$; wherein f is the frequency, n is the order of the derivative $\overline{\psi}$ and is the Fourier transform of the wavelet; —the normalization factor is calculated for each frequency by adjusting a Gaussian noise model over the central portion of the bar chart of the real coefficients; —the threshold is defined by the following formula:

$$thr \equiv x | lFDR(x) = H_0(x)/H_G(x) < Q$$

wherein thr is the threshold, Q is the acceptable error rate, $H_0$ is the null hypothesis and $H_G$ is the total distribution; —the method further comprises a step of determining the time and frequency range of the local maxima; —the method further comprises a step of classifying the elements of interest as transient or oscillation; the method further comprises a step of viewing elements of interest in the time-frequency domain and/or the time domain; and—the detector comprises a classifier.

BRIEF DESCRIPTION OF THE FIGURES

The invention shall be better understood when reading the following non-limiting description, written with regard to the accompanying drawings, wherein.

DETAILED DESCRIPTION OF THE INVENTION

The method of detection according to the invention is a method for representing and automatically detecting elements of interest in electrophysiological signals. These signals are biological/physical plots, regardless of their origin.

In a first step of the method according to the invention, electrophysiological signals are delivered. These signals are intracranial signals and, in particular, are stereo-electroencephalographic signals (SEEG) noted as f. These are complex signals comprising low and high frequency oscillations and points or transients. These oscillations, points and transients are the elements/events of interest which are detected according to the method according to the invention.

In light of this detection, a whitened time-frequency representation of said electrophysiological signals is produced. In other words, the signals are rectified while still retaining a good signal-to-noise ratio for the elements of interest.

The whitening is carried out in the time-frequency domain then applied to the time domain for the viewing.

For the carrying out of the whitened time-frequency representation, a continuous wavelet transform is applied (CWT) noted as T to said signals. This T transform is calculated using the following formula:

$$T_f(b, \alpha) = \frac{1}{\sqrt{\alpha}} \int_{-\infty}^{+\infty} f(t) \overline{\psi\left(\frac{t-b}{\alpha}\right)} dt$$

wherein $\psi$ is the wavelet, $\alpha$ the dilation factor, b the translation factor and t is the time. The wavelet chosen is a Gaussian derivative wavelet (DoG), analytical. Its analytical properties make it possible to reconstruct the signal, contrary to Morlet wavelets, and as such obtain the whitened signal in the time domain such as will be specified in the rest of this description according to the invention. Its expression in the frequency domain is as follows:

$$\overline{\psi}(f) = f^n \exp(-f^2) \text{ for } f \geq 0 \text{ and } f \geq 0 \text{ and } = 0 \text{ for } f < 0$$

Once the wavelet coefficients are obtained, they are standardized in order to make it possible to bring out the elements of interest better and, in particular, the high-frequency oscillations. This corresponds to a step according to the invention according to which the time-frequency representation of the signals is standardized, in order to obtain a whitened/standardized representation.

The standardization chosen is a standardization referred to as $Z_{HO}$ or $H_0$ Z-score. This standardization allows for an optimum representation of the high-frequency oscillations, without reducing the signal-to-noise ratios or losing the content of the low frequencies. Contrary to conventional methods, the power of the background activity at each frequency is estimated directly over the data of interest and does not require the difficult defining of a baseline. Concretely, a Gaussian noise model is adjusted over the central portion of the bar chart of the real coefficients at each frequency. Then the coefficients are transformed into z by the following formula:

$$T^i_{f,z_{n_0}}[n, m] = \frac{T^i_f[n, m] - \mu[m]}{\sigma[m]}.$$

where n and m are respectively the time and frequency indexes,
$T^i_f.Z_{H_0}$ and $T^i_f[n,m]$ are the coefficient i (real or imaginary) for the indexes n and m after and before standardization, $\mu[m]$ and $\sigma[m]$ correspond to the means and the standard deviation of the estimated Gaussian at the frequency of index m. The standardization transforms the background activity into a white noise in order to balance the power of the activities through the frequencies. The spectrum is therefore whitened. In addition, it makes possible the optimum representation of the whitened signal both in the time-frequency domain and in the time domain. This standardization places on the same scale all of the distributions of the real and imaginary coefficients by frequency.

Figure 1A:
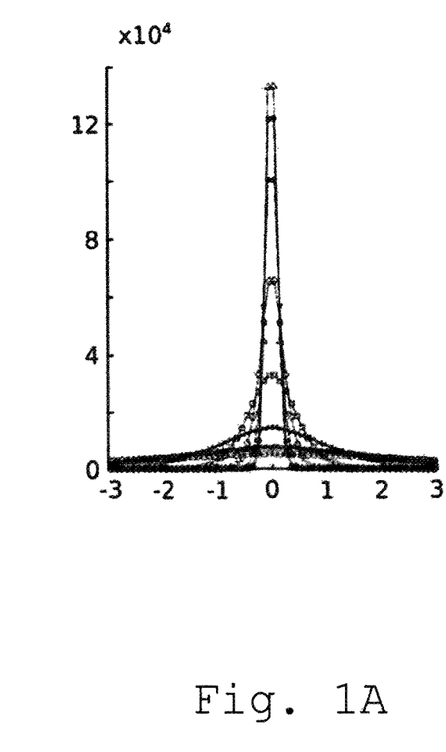
FIGS. 1A to 1C are bar charts that show the distributions of the real part of the wavelet coefficients at different frequencies, without standardization or with a standardization and in particular with a standardization according to the method according to the invention.
Figure 1B:
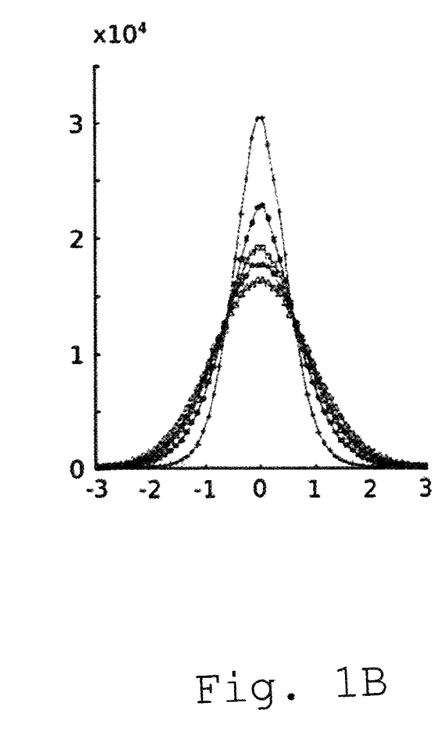
Figure 1C:
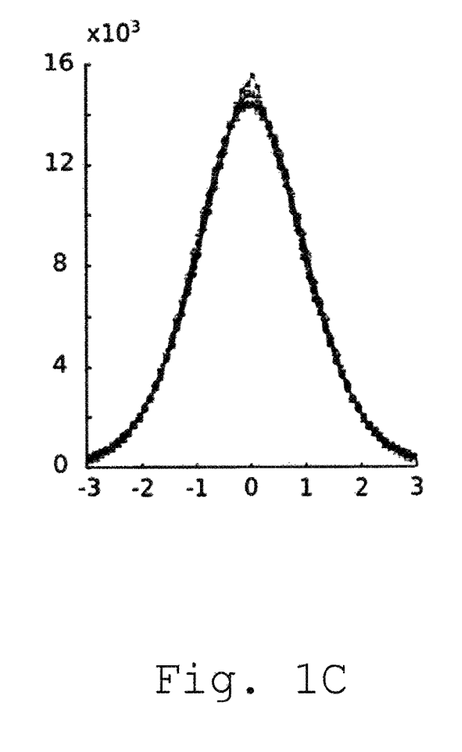

FIGS. 1A to 1C show bar charts that show, for different frequencies, the distributions of the real part of the wavelet coefficients at different scales, without standardization or with a standardization and, in particular, with the standardization $Z_{HO}$. In FIG. 1A, the distributions of the real part of the wavelet coefficients are not standardized. Note a large difference in width between the distributions. In FIG. 1B, the distributions are standardized with the mean and the standard deviation—$\mu[\alpha]$ and $\sigma[\alpha]$—estimated over all of the distributions. A difference between the widths of the distributions is still noted. In FIG. 1C, the distributions are standardized by means of the aforementioned standardization $Z_{HO}$. This time, all of the distributions have the same range through the frequencies.

In order to obtain the whitened time-frequency representation, according to the invention, the square modulus of the wavelet coefficients is calculated after having standardized the real and imaginary parts thereof.

Figure 2A:
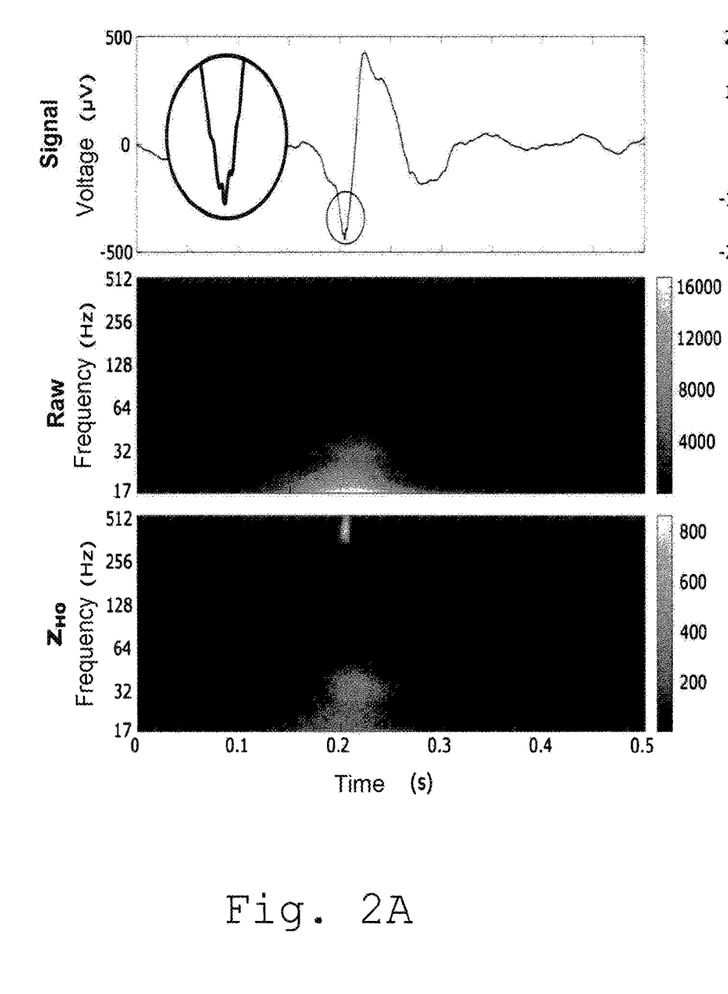
FIGS. 2A and 2B each show an example of high-frequency oscillations recorded in an epileptic patient by carrying out a whitened time-frequency representation according to the method according to the invention.
Figure 2B:
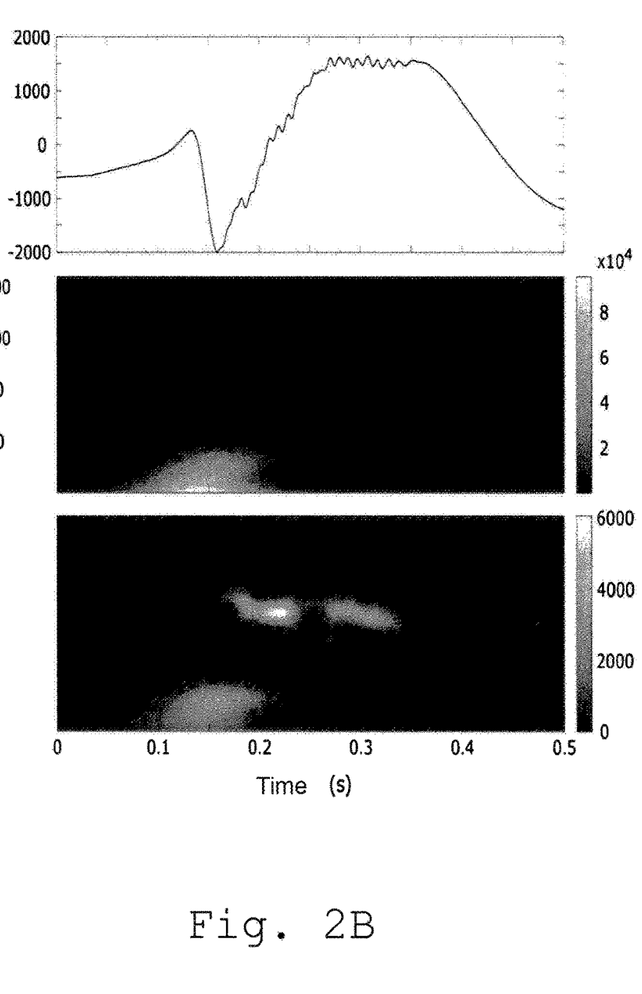

FIGS. 2A and 2B each show an example of high-frequency oscillations recorded in an epileptic patient. For each example, the top line shows a signal comprising elements of interest in the time domain, the intermediate line shows the associated raw time-frequency representation, and the bottom line shows the whitened time-frequency representation by means of the standardization referred to as $Z_{HO}$. In FIG. 2A, the oscillations are FR oscillations. In FIG. 2B, the oscillations are HG oscillations. On the top line of FIG. 2A, the insert corresponds to a zoom on the high-frequency FR oscillations. It appears that the high-frequency oscillations are difficult to identify on the lines at the top and the intermediate lines. However, they appear clearly on the bottom line, thanks to the standardization $Z_{HO}$.

As the distribution of the real part of the coefficients is identical through the frequencies, it is possible to study them at the same time and to apply a single threshold based on the local false discovery rate (lFDR Efron 2005). According to another step according to the invention, a threshold is therefore set.

The lFDR is an empirical Bayes approach that assumes that the noise $H_0$ composes most of the center of the distribution $H_G$ and that the rest of the distribution $H_1$ is produced by the signal of interest. The threshold is defined in the following formula:

$$thr \geq x | lFDR(x) = H_0(x)/H_G(x) < Q$$

wherein thr is the threshold, Q is the acceptable error rate, $H_0$ is the null hypothesis and $H_G$ is the total distribution.

In practice, two thresholds are obtained. This entails a first threshold $thr^-$ for the negative portion and a second threshold $thr^+$ for the positive portion. The threshold of the lFDR is:

$$thr_{lFDR} = \frac{thr^+ - thr^-}{2}$$

By studying the bar charts of the real coefficients of the human background activity (Real Human Background, BKG), it is noted that these distributions are described by a Gaussian. The central portion of the bar chart of the $T^i_f.Z_{H_0}$ taken as a whole can then be modeled by a reduced centered Gaussian and the error rate Q is left to the appreciation of the user.

Figure 3:
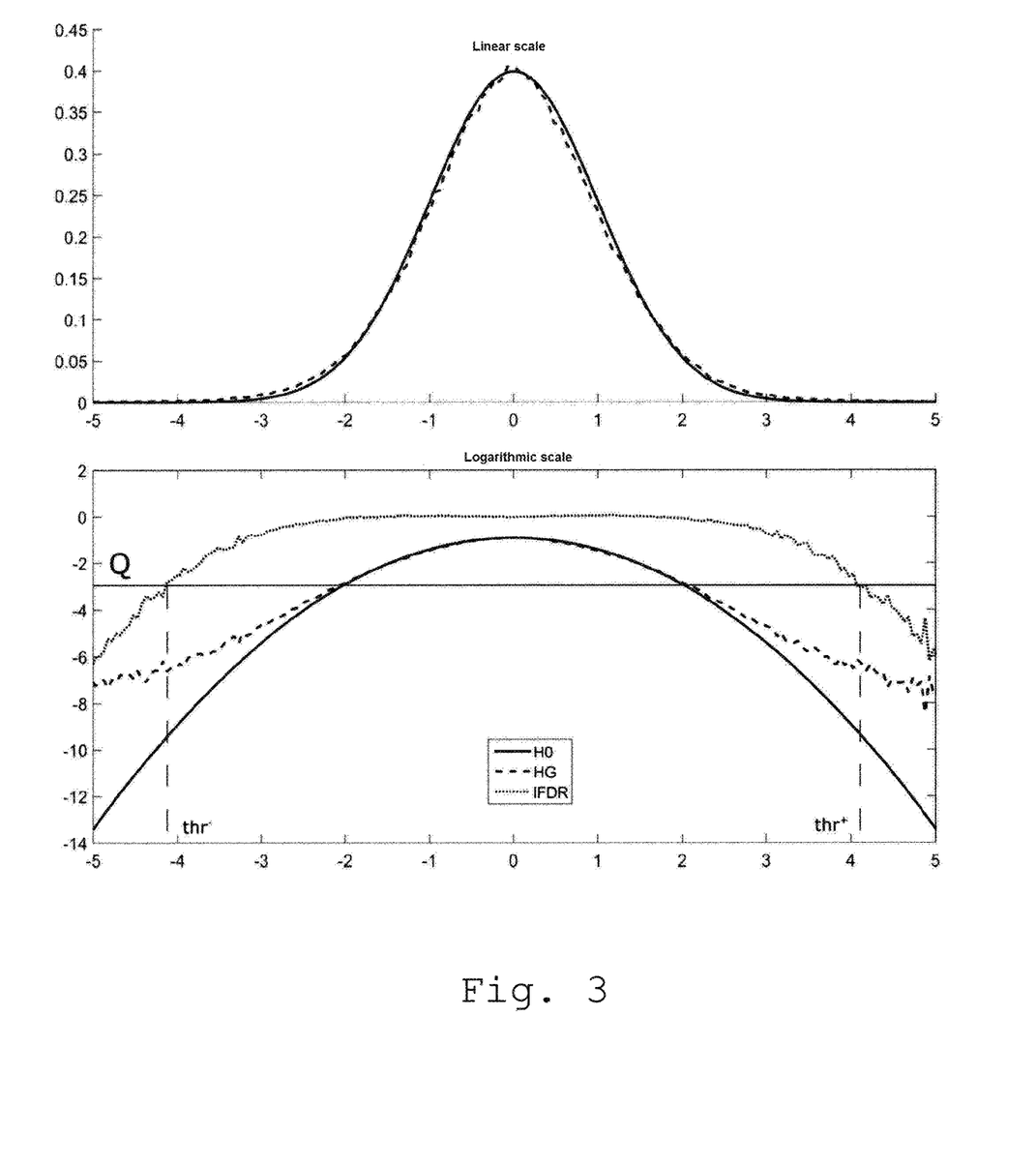
FIG. 3 shows the application of the lFDR for the implementing of the method according to the invention.

An illustration of the application of the lFDR is shown in FIG. 3. In this figure, the total distribution HG, the null hypothesis $H_0$ as well as the lFDR are represented as dashed, solid black and dotted strokes, respectively. The threshold on the error rate Q is represented by a solid horizontal line. The thresholds thr+ and thr− are obtained at the intersection of the lFDR and of Q.

According to another step of the method according to the invention, the threshold is applied to the standardized time-frequency representation. To this effect, the threshold obtained thanks to the lFDR is squared:

$$\text{thr}_{Z_{HO}} = \text{thr}_{lFDR}^2$$

It is then possible to detect, in the standardized time-frequency representation, the local maxima which are higher or equal to the applied threshold, and which correspond to elements of interest that come out of the noise. Thanks to the whitening of the data and to the study of the events in time-frequency, the points and the oscillations are detected, whether or not they occurred at the same time.

In practice, this detection consists in selecting all of the local maxima which are higher than the threshold set by the lFDR. The local maxima are relative to events located both in time and in frequency as are the oscillations sought. It is then possible to have the time of occurrence as well as the oscillation frequency. The epileptic points are also located in time-frequency, but are more spread out in frequency and less spread out in time than the oscillations and their local maximum is lower than the frequency band of the high-frequency oscillations. Inversely, artifacts of the Dirac type do not produce local maxima and therefore are not detected. In reality, an artifact mixed with noise or a very brief transient with an oscillation can sometimes create erroneous local maxima at high frequency. However, as the detections are made in the theoretical framework of wavelets, the width of the blob relative to the local maximum can be compared with the theoretical width of the blob which would have been generated by a Dirac peak. This makes it possible to differentiate a brief element (i.e. an epileptic point or a brief transient) in relation to an oscillation regardless of its frequency. In addition, as the frequency width of the wavelets is constant on a logarithmic scale, it is also possible to distinguish the oscillations that still have a limited frequency width regardless of their frequency, transients that have a frequency width that is more extended.

Figure 4A:
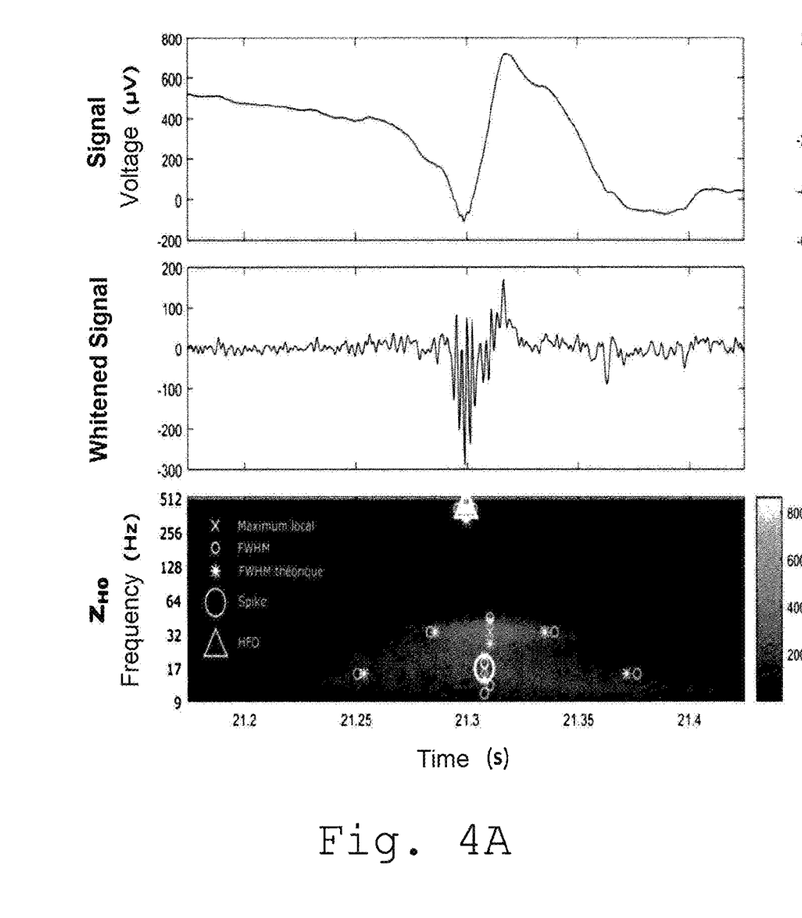
FIGS. 4A and 4B show two examples of detection according to the method according to the invention in the time domain with the signal and the whitened reconstruction thereof (first and second line, respectively) as well as in the whitened time-frequency domain (third line)
Figure 4B:
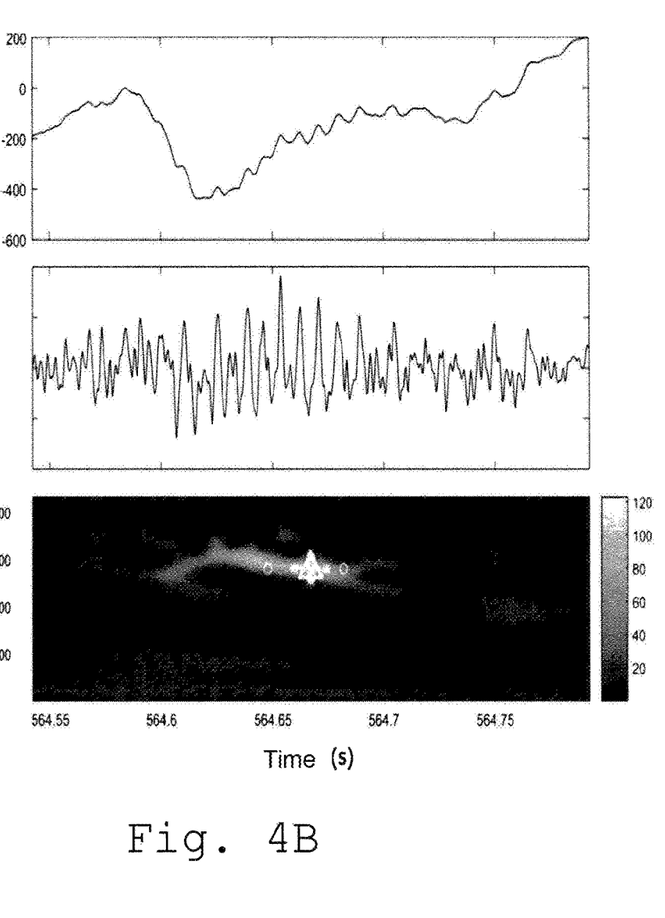

Two examples of detection are shown in FIGS. 4A and 4B. In this figure, the crosses correspond to the local maxima higher than the threshold, the white circles to the measured width at mid-height (Full Width at Half Maximum, FWHM), the asterisks to the theoretical width at mid-height, the large circle to an epileptic point (spike) and the triangle to a high-frequency oscillation. It appears that the theoretical time width is very close to the measured time width for one point.

The method according to the invention therefore makes it possible to view and to identify several types of physiological activities such as high-frequency oscillations, the epileptic points and the oscillations of lower frequency. The parameters used to classify the events do not depend on frequencies. Thanks to this method, the identification of the cerebral zones producing high-frequency oscillations is facilitated, as it is automatic.

Note that the combined steps of standardization and of the lFDR make it possible to differentiate the background activity of the elements of interest and ensure their authenticity. The combination of these two steps also makes it possible to detect the high-frequency oscillations that would have been rejected because they are not visible in the original signal. In addition, each oscillation will be labeled by a frequency. It is as such possible to determine the physiological and pathological frequency bands for the patients which was not possible with the other detectors. Note that the method does not presuppose a cutting into frequency bands.

Figure 5A:
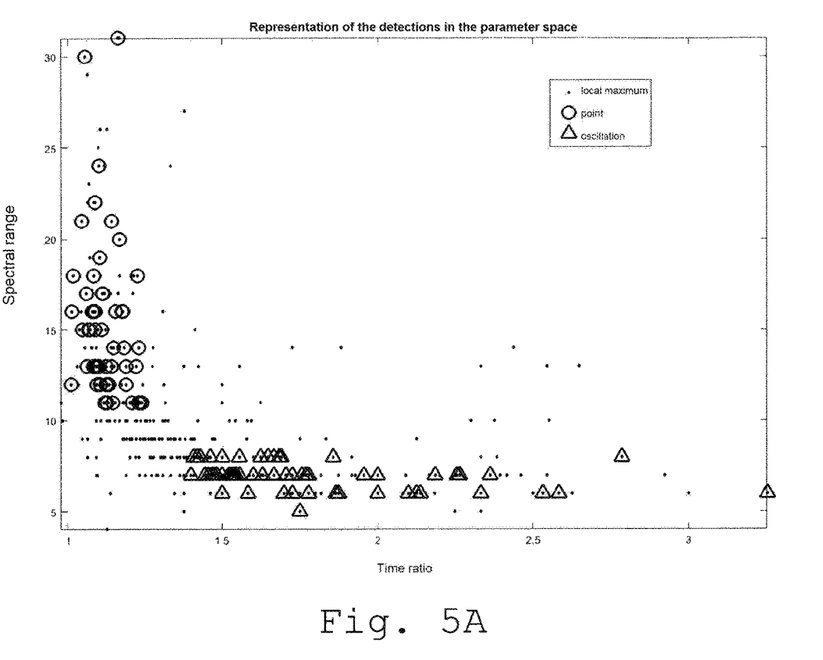
FIGS. 5A and 5B show the detections in the space of parameters and the distribution of the frequencies of the oscillations according to the invention.

In FIG. 5A, all of the detections are represented by a point of coordinates, their frequency range and their time ratio. A threshold on the limit of duration, equivalent to the number of oscillations, and on the spectral range makes it possible to separate the oscillations of the epileptic points and non-oscillating events, i.e. comprising less than 3 or 4 oscillations. The oscillations, the epileptic points and the non-oscillating events are illustrated by points. The detections selected as points and as oscillations are respectively represented by circles and triangles.

Figure 5B:
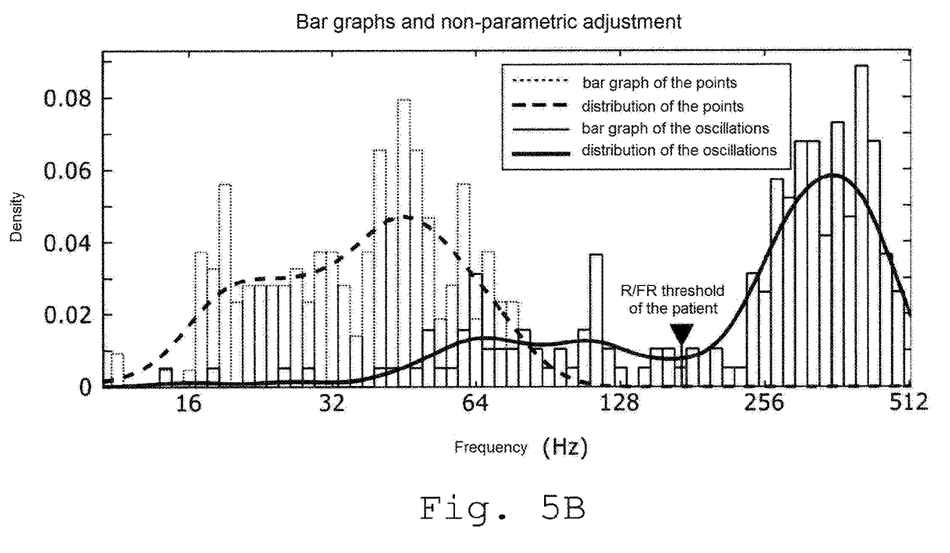

The bar charts of the frequencies of the points and of the oscillations detected are shown in FIG. 5B. A non-parametric adjustment is carried out in a dashed line for the points and in a solid black line for the oscillations. Note that the zone studied produces substantially more high-frequency oscillations than low-frequency oscillations. Thanks to this representation, it can be realized that it would be more interesting to place the cut-off of the oscillations R/FR at 170 Hz rather than to take as a mark the conventionally defined bands R and FR.

Figure 6A:
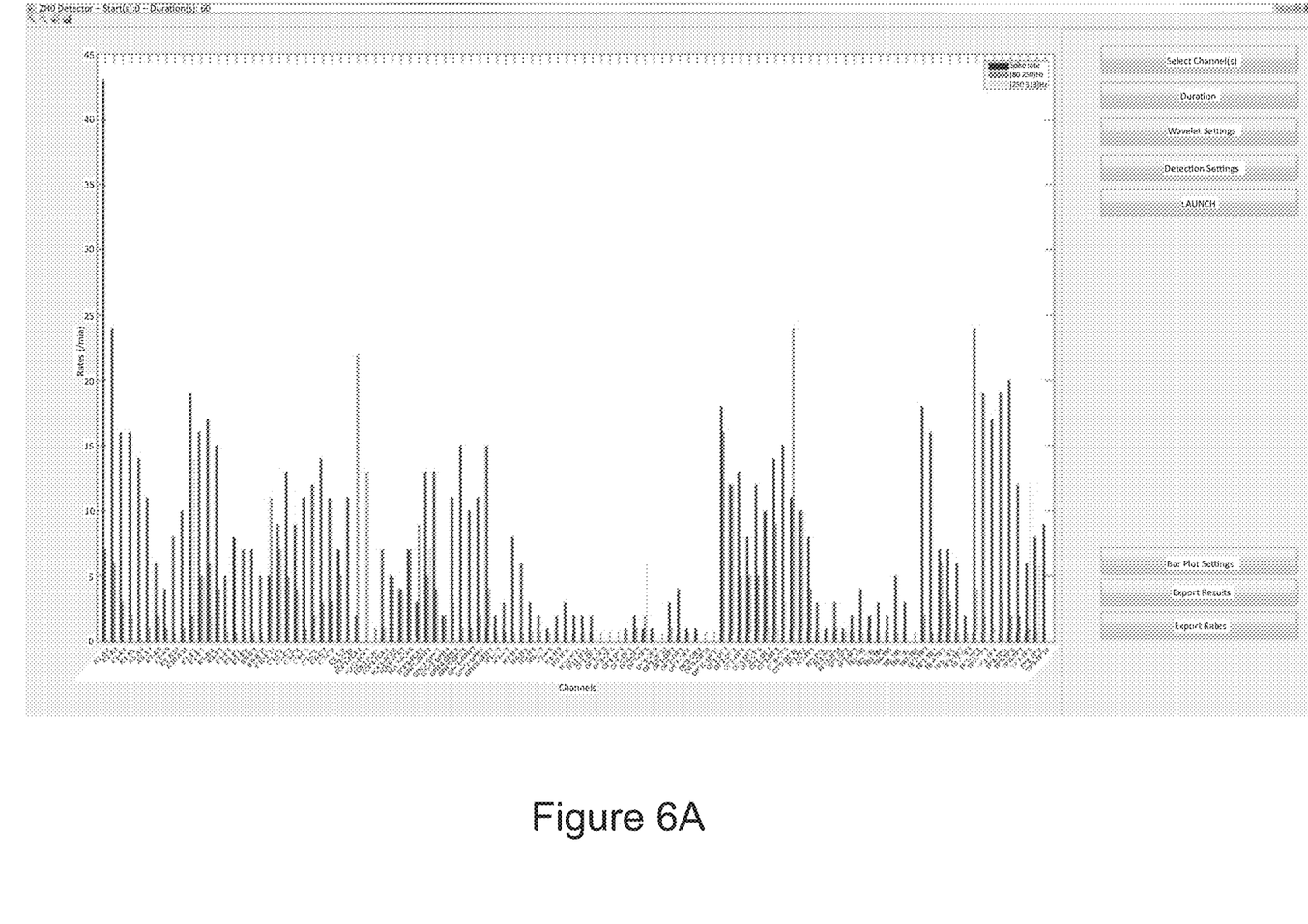
FIGS. 6A and 6B show an example implementation of the detector and of the simultaneous viewing of the signal in the time domain with the original signal and the whitened reconstruction thereof as well as in the whitened time-frequency domain, in the daily clinical use according to the invention.
Figure 6B:
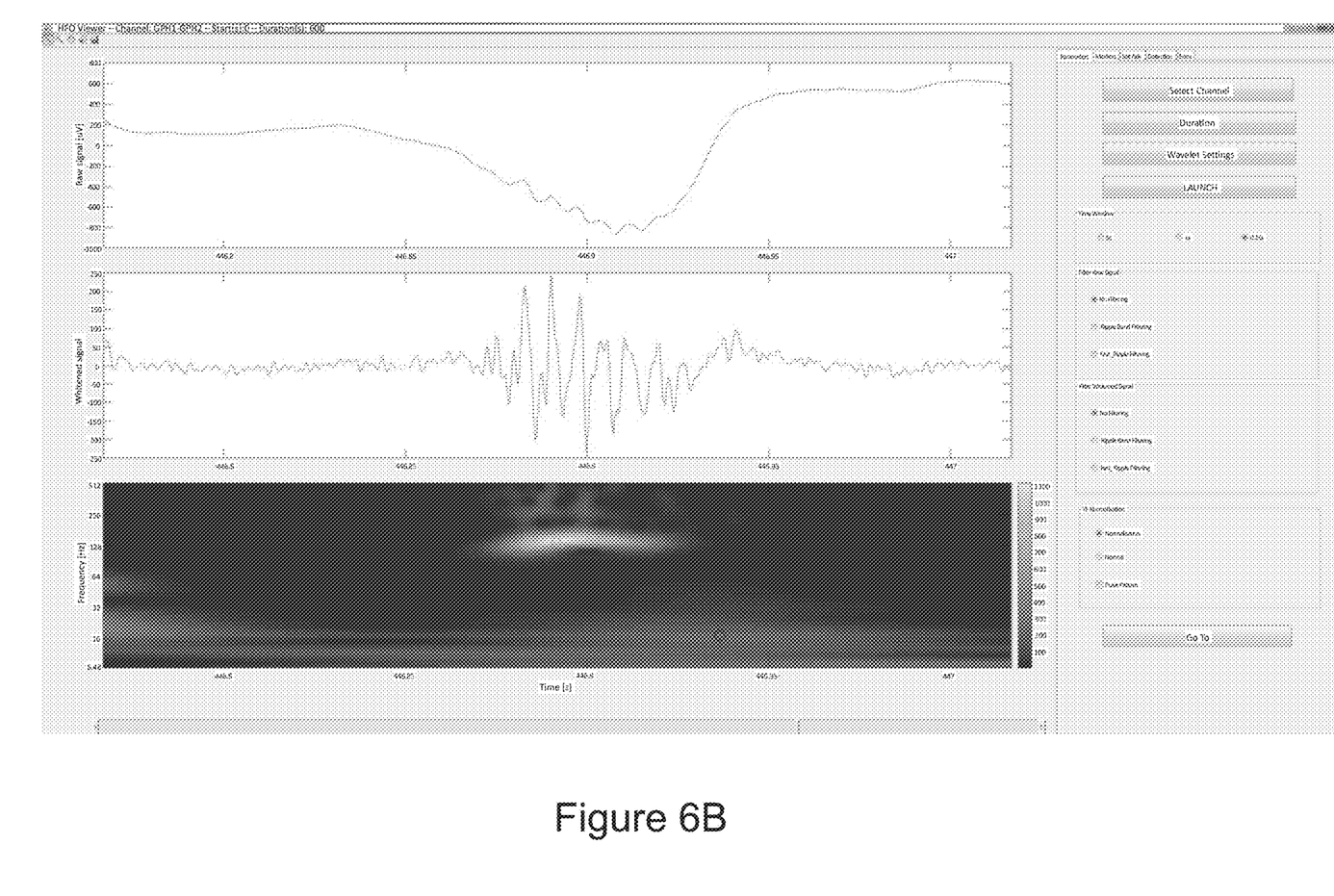

The detector according to the invention can be implemented in a software such as the AnyWavem software in the form of an extension module (plugin) for regular clinical use. This software platform is described for example in the document entitles "AnyWave: a cross-platform and modular software for visualizing and processing electrophysiological signals", Colombet et al., Journal Neurosciences Methods, March 2015, 242, 118-26. The plugin is comprised of two elements, an interface (FIG. 6A) that makes it possible to select several channels of the various electrodes and to run the detector as well as to show the results in the form of a diagram of the detection rates of the epileptic points and of the oscillations by frequency bands chosen by the user, and a second interface (FIG. 6B) that makes it possible to view the signal of a channel synchronously in the time domain and in the standardized time-frequency domain and to display the signal in the detection time obtained previously: simultaneous viewing of the signal in the time domain with the original signal and the whitened reconstruction thereof as well as in the whitened time-frequency domain. Each plugin communicates with the software in order to acquire the signals and their information. The software comprising the plugin is intended to be implemented by a workstation, possibly in liaison with a server, in a conventional IT environment of the Windows™ type. The workstation comprises at least one memory wherein the software will be recorded, a processor for the execution thereof, and a screen for displaying the results. The detection is automatic. The implementation of the method does not require the presence of a qualified person from a medical standpoint.

The invention claimed is:

1. A method for automatically detecting elements of interest in electrophysiological signals comprising:
   delivering electrophysiological signals;
   producing a whitened time-frequency representation of the electrophysiological signals;
   setting a threshold;
   applying the threshold to the whitened time-frequency representation;
   detecting, in the whitened time-frequency representation, local maxima that are higher than or equal to the threshold,
   wherein the producing of the whitened time-frequency representation comprises:
   (i) applying a continuous wavelet transform, (ii) separately standardizing real parts and imaginary parts of wavelet coefficients of the continuous wavelet transform, wherein the standardizing comprises calculating a normalization factor for each frequency of the whitened time-frequency representation by providing a bar chart showing the real parts of the wavelet coefficients, and adjusting a noise model over a central portion of the bar chart, and (iii) after the standardizing, calculating a square modulus of the standardized real parts and imaginary parts of the wavelet coefficients.

2. The method according to claim 1, wherein the electrophysiological signals are intracranial signals.

3. The method according to claim 2, wherein the intracranial signals are stereo-electroencephalographic signals.

4. The method according to claim 1, wherein the elements of interest include at least one selected from the group consisting of (i) low frequency oscillations, (ii) high frequency oscillations, and (iii) points.

5. The method according to claim 4, wherein the continuous wavelet transform is calculated from the following formula:

$$T_f(b, \alpha) = \frac{1}{\sqrt{\alpha}} \int_{-\infty}^{+\infty} f(t)\overline{\psi\left(\frac{t-b}{\alpha}\right)}dt$$

wherein f is the electrophysiological signals, T is the continuous wavelet transform, $\psi$ is a wavelet, $\alpha$ is a dilation factor, b is a translation factor and t is time.

6. The method according to claim 4, wherein a wavelet chosen is a Gaussian derivative wavelet (DoG), analytical and an expression of the wavelet in a frequency domain is as follows:

$\tilde{\psi}(f)=f^n \exp(-f^2)$ for $f \geq 0$ and $=0$ for $f<0$ wherein f is frequency, n is an order of derivative and $\tilde{\psi}$ is a Fourier transform of the wavelet.

7. The method according to claim 4, wherein the noise model is a Gaussian noise model.

8. The method according to claim 1, wherein the threshold is defined by the following formula:

thr=x||FRD(x)=$H_0(x)/H_G(x)<Q$ wherein thr is the threshold, Q is an acceptable error rate, $H_0$ is a null hypothesis and $H_G$ is a total distribution.

9. The method according to claim 1, further comprising determining a time and a frequency range of the local maxima.

10. The method according to claim 1, further comprising classifying the elements of interest as transient or oscillation.

11. The method according to claim 1, further comprising viewing elements of interest.

12. The method according to claim 2, wherein the elements of interest include at least one selected from the group consisting of (i) low frequency oscillations, (ii) high frequency oscillations, and (iii) points.

13. The method according to claim 12, wherein the continuous wavelet transform is calculated from the following formula:

$$T_f(b, \alpha) = \frac{1}{\sqrt{\alpha}} \int_{-\infty}^{+\infty} f(t)\overline{\psi\left(\frac{t-b}{\alpha}\right)}dt$$

wherein f is the electrophysiological signals, T is the continuous wavelet transform, $\psi$ is a wavelet, $\alpha$ is a dilation factor, b is a translation factor and t is time.

14. The method according to claim 3, wherein the elements of interest include at least one selected from the group consisting of (i) low frequency oscillations, (ii) high frequency oscillations, and (iii) points.

15. The method according to claim 14, wherein the continuous wavelet transform is calculated from the following formula:

$$T_f(b, \alpha) = \frac{1}{\sqrt{\alpha}} \int_{-\infty}^{+\infty} f(t)\overline{\psi\left(\frac{t-b}{\alpha}\right)}dt$$

wherein f is the electrophysiological signals, T is the continuous wavelet transform, $\psi$ is a wavelet, $\alpha$ is a dilation factor, b is a translation factor and t is time.

16. The method according to claim 5, wherein the wavelet chosen is a Gaussian derivative wavelet (DoG), analytical and its expression in the frequency domain is as follows:

$\tilde{\psi}(f)=f^n \exp(-f^2)$ for $f \geq 0$ and $=0$ for $f<0$ wherein f is frequency, n is an order of derivative and $\tilde{\psi}$ is a Fourier transform of the wavelet.

17. The method according to claim 5, wherein the noise model is a Gaussian noise model.

18. The method according to claim 5, wherein the wavelet coefficients are standardized by the following formula:

$$T^i_{f,Z_{H_0}}[n, m] = \frac{T^i_f[n, m] - \mu[m]}{\sigma[m]}$$

where n is a time index and m is a frequency index, $T^i_{f,Z_{H_0}}$ and $T^i_f[n,m]$ are real or imaginary coefficient for n and m after and before standardization, $\mu[m]$ and $\sigma[m]$ correspond to a mean and a standard deviation of an estimated Gaussian at a frequency of the frequency index m.

19. A detector for the automatic detection of elements of interest in electrophysiological signals, wherein the detector comprises a non-transitory software-recording medium on which a software in the form of an extension module is recorded, wherein the software, when executed by a computer, implements a method comprising:

delivering electrophysiological signals;

producing a whitened time-frequency representation of the electrophysiological signals;

setting a threshold;

applying the threshold to the whitened time-frequency representation;

detecting, in the whitened time-frequency representation, local maxima that are higher than or equal to the threshold, wherein the producing of the whitened time-frequency representation comprises:

(i) applying a continuous wavelet transform, (ii) separately standardizing real parts and imaginary parts of wavelet coefficients of the continuous wavelet transform, wherein the standardizing comprises calculating a normalization factor for each frequency of the whitened time-frequency representation by providing a bar chart showing the real parts of the wavelet coefficients, and adjusting a noise model over a central portion of the bar chart, and (iii) after the standardizing, calculating a square modulus of the standardized real parts and imaginary parts of the wavelet coefficients.

20. The detector according to claim 19, comprising a classifier.

21. A method of automatic detection of elements of interest in electrophysiological signals of an epileptic patient, comprising applying a detector according to claim 19 to detect the elements of interest in the electrophysiological signals of the epileptic patient.

22. The device according to claim 19, wherein the noise model is a Gaussian noise model.

23. The device according to claim 19, wherein the wavelet coefficients are standardized by the following formula:

$$T^i_{f,Z_{H_0}}[n,m] = \frac{T^i_f[n,m] - \mu[m]}{\sigma[m]}$$

where n is a time index and m is a frequency index, $T^i_{f,Z_{H_0}}$ and $T^i_f[n,m]$ are real or imaginary coefficient for n and m after and before standardization, $\mu[m]$ and $\sigma[m]$ correspond to a mean and a standard deviation of an estimated Gaussian at a frequency of the frequency index m.

* * * * *